United States Patent [19]
Eisenberg et al.

[11] Patent Number: 4,792,145
[45] Date of Patent: Dec. 20, 1988

[54] ELECTRONIC STETHOSCOPE SYSTEM AND METHOD

[75] Inventors: Lawrence Eisenberg, New York, N.Y.; Michael Eisenberg, Cambridge, Mass.

[73] Assignee: Sound Enhancement Systems, Inc., New York, N.Y.

[21] Appl. No.: 914,027

[22] Filed: Oct. 6, 1986

Related U.S. Application Data

[63] Continuation-in-part of Ser. No. 795,059, Nov. 5, 1985, abandoned.

[51] Int. Cl.$^4$ .............................................. A61B 7/04
[52] U.S. Cl. .................................. 128/715; 128/773; 381/67
[58] Field of Search ............................. 128/660–663, 128/715, 773, 701; 381/67, 98

[56] References Cited

U.S. PATENT DOCUMENTS

| | | | |
|---|---|---|---|
| 4,424,815 | 1/1984 | Kuntz | 128/715 |
| 4,509,526 | 4/1985 | Barnes et al. | 128/663 |
| 4,534,361 | 8/1985 | Berger et al. | 128/680 |
| 4,594,731 | 6/1986 | Lewkowicz | 381/67 |

*Primary Examiner*—Maryann Lastova
*Attorney, Agent, or Firm*—Pennie & Edmonds

[57] ABSTRACT

A microprocessor based sound enhancement system in which frequencies outside of the auditory range of the human ear are translated into sound within the auditory range by translating each frequency component of the entire frequency spectrum of the input signal by a time scale compression factor. Preferably, a microprocessor transforms an electrical signal corresponding to the input signal into a frequency spectrum signal comprising frequency components having frequency, phase, and amplitude elements by performing a fast Fourier transform (FFT) operation on the input signal. The frequency components of this transformed signal are translated and the resulting translated frequency spectrum signal is transformed into a time varying output signal by performing an inverse FFT operation on the translated frequency spectrum signal. When heart pulses or similar periodic waveforms are monitored, the pulse rate of the signal is maintained in the output signal. Alternatively, the time varying signal is compressed in the time scale and then transformed into audible sound, while maintaining the original pulse rate in the output signal, thereby resulting in the same output signal as that resulting from translating the entire frequency spectrum by the time scale compression factor.

18 Claims, 8 Drawing Sheets

TO FIG. 5b

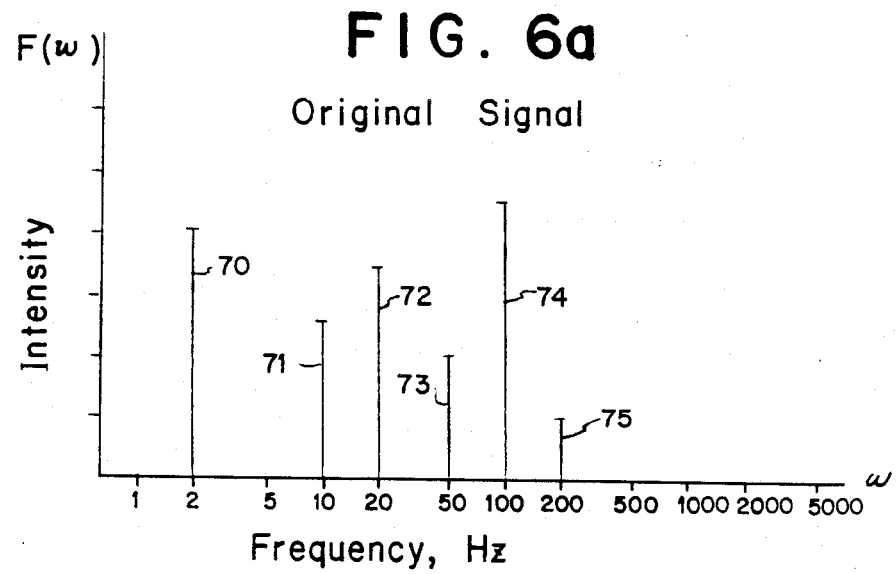
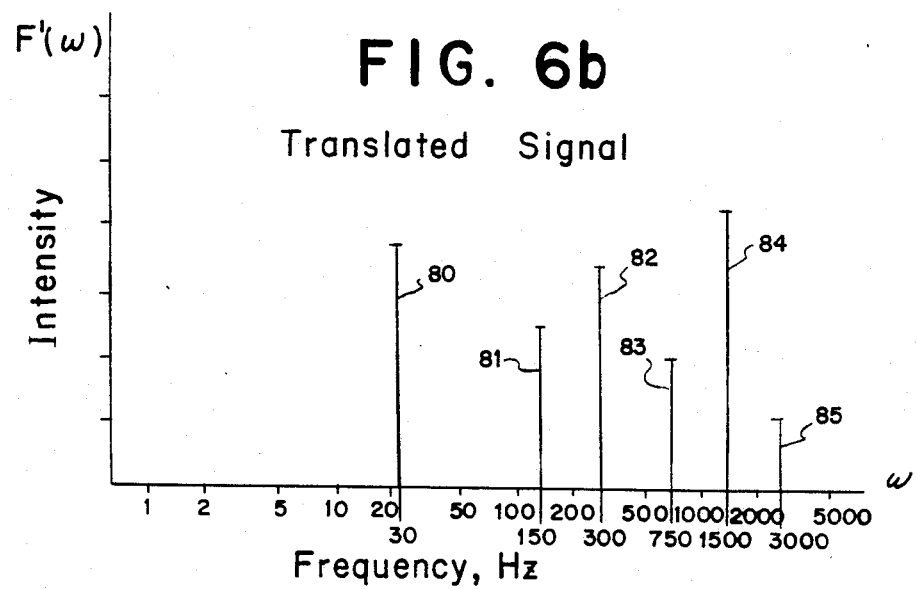

Original Signal

Translated (Time-Compressed) Signal

ELECTRONIC STETHOSCOPE SYSTEM AND METHOD

RELATED APPLICATIONS

This is a continuation-in-part of co-pending application titled "Sound Enhancement System," Ser. No. 795,059, filed Nov. 5, 1985, now abandoned.

FIELD OF INVENTION

The present invention relates to the enhancement of sound having frequency components that are not within the auditory range of the human ear so that these frequency components become audible without altering the tonal relationship among these frequency components.

BACKGROUND OF THE INVENTION

Since the nineteenth century, it has been well known by physicians that a medical diagnosis can be determined by listening to the sounds emanating from a patient's internal organs either in operation or as a result of a physician's rapping on the patient's chest with his fingers. This method of medical diagnosis is known as auscultation. In order to amplify these sounds, the stethoscope was invented in 1816 by the French physician Rene Laennec and has since proven to be an invaluable tool in noninvasive medical diagnosis.

Auscultation is considered by many cardiological authorities to be the most sensitive test of the functional integrity of the heart. Not infrequently, murmurs or changes in the heart sounds are the only concrete indication of heart disease. The ability to distinguish between what is normal and what is abnormal is particularly difficult in many borderline cases.

Cardiovascular sounds, however, include components that have frequencies and intensities which are not within the auditory range of the human ear. As a result, only a small fraction of these sounds or acoustic vibrations can be heard using a conventional stethoscope. There have been attempts to solve the problem of low signal levels by the use of electronic stethoscopes using microphones and signal amplifiers. However, the use of such equipment is limited in frequency due to inherent insensitivity o the human ear, as well as the earphones used in these electronic stethoscopes.

Electronic stethoscopes have been devised which enable a user to hear heart sounds more easily. For example, U.S. Pat. No. 4,528,689 discloses an electronic stethoscope which provides a signal which is similar to but not exactly the same as a slowed down version of the original sound by producing an output signal which is composed of replicated sets of cycles of the original sound. The output signal, however, does not maintain the tonal relationships of the original sounds, is not a truly frequency shifted version of the original sound, and is merely the original signal periodically reproduced so as effectively to have a longer duration.

Other electronic stethoscopes have been devised which shift low frequency signals into a frequency within the ear's audible range, however, such prior art devices all have their limitations.

For example, U.S. Pat. No. 3,562,428 discloses an electronic stethoscope which modulates the detected sound so that low frequency signals are shifted into the audible frequency range. The quality of the sound generated by this stethoscope is substantially different from the usual sounds heard by the physician since a carrier signal is added to the originally detected sound whereby the detected sound is merely shifted into a higher frequency range without maintaining the same tonal relationships as in the originally detected sound.

U.S. Pat. No. 4,220,160 is directed to a device for transposing heart sounds into the audible frequency range by processing certain predetermined frequency components of the detected sound to obtain an output signal which consists of the sum and difference of the frequency components and a carrier frequency signal. The output signal is then filtered to remove the difference between the frequency components.

U.S. Pat. No. 4,594,731 discloses an electronic stethoscope in which the detected heart sounds are frequency multiplied to transpose the sounds to a more favorable position within the auditory range. The signal is input to a frequency doubling circuit consisting of a full wave rectifier, bandpass filter and a wave shaping circuit.

The main disadvantage to these prior art electronic stethoscopes is that the tonal relationships in the sounds generated by the electronic stethoscopes are different from the tonal relationships in the original sounds and thus do not blend in the same way. For example, a group of tones that are separated by octaves (Two signals are said to be separated by an octave if the ratio of their frequencies is equal to two.) in the original sound (10 Hz, 20 Hz, and 40 Hz) would no longer be separated by octaves in the signal after processing by the electronic stethoscopes because the detected signal is merely shifted to a different frequency range (110 Hz, 120 Hz, and 140 Hz). Thus the sounds generated by such electronic stethoscopes are not similar to the original sounds, do not combine with each other in the same way as the original sounds, and are unrecognizable to experienced physicians trained to recognize the sounds of a conventional stethoscope. Similar problems arise using the electronic stethoscopes in which the frequencies of the sound are simply multiplied by a constant value. It is important that not only the relative frequency relationships between signal components be maintained, but also the relative phase relationships as well as the amplitude of the signal components. The frequency multiplication circuitry described in U.S. Pat. No. 4,598,731 not only does not maintain the relative phase relationships of the frequency components, as well as the amplitudes but also generates new unwanted frequency components. This combination changes the shape of the waveform and the melody of the heart sounds so that they are no longer recognizable as a transposed version of the original heart sounds.

SUMMARY OF THE INVENTION

In the microprocessor based electronic stethoscope system of the present invention, heart sounds with frequencies that are not within the auditory range of the human ear are detected and transformed into an electrical input signal. The time varying signal is compressed in the time scale while maintaining the original pulse rate whereby the relative frequency and phase relationships of the signal are preserved. The output signal is transformed into an audible sound that has the same melody as the original heart sound, but at a higher pitch and includes those frequencies which were previously inaudible to the human ear.

In one embodiment of the present invention the microprocessor transforms the electrical input signal into a frequency spectrum signal by performing a fast Fourier transform (FFT) on the signal. Each component of the spectrum is then translated in frequency by a constant time scale factor whereby the original inter-component frequency and phase relationships of the signal are maintained. An inverse FFT operation is used to translate the frequency spectrum signal into a time varying signal which is subsequently transformed into audible sound.

In another embodiment of the present invention the input electrical signal is sampled at a first sampling rate and is output at a second faster sampling rate to translate the inaudible sounds into the audible frequency range.

In the present invention, sounds having frequencies outside the auditory range of the human ear are brought into the auditory range without changing the tonal relationship among the frequency components of the sounds. In other words, the translated sounds maintain the melody of the original heart sounds but at a higher pitch to include those sounds which were originally inaudible.

By using the system of the present invention to translate inaudible sounds into the audible frequency range, the tonal relationships of the sounds remain unchanged because amplitudes as well as the relative frequency and phase relationships of the frequency components of the signal are maintained. For example, a group of tones separated by octaves (10 Hz, 20 Hz, and 40 Hz) when time compressed in accordance with the present invention results in tones (100 Hz, 200 Hz, and 400 Hz) which remain separated by octaves and have the same relative phase relationships. This output sound is similar to the original sound since the new tones combine with each other in the same way as the original sounds and thus remain recognizable to physicians experienced in using conventional stethoscopes.

By choosing the appropriate time compression factor, sounds having frequencies above the auditory range as well as sounds having frequencies below the auditory range can be translated into the auditory range.

Although the sound enhancement system of the present invention is designed primarily for the detection and analysis of cardiovascular sounds, other sounds generated by the human body can also be enhanced. Among the sounds that can be monitored are bowel sounds as in the diagnosis of acute appendicitis, brachial artery sounds, carotid artery sounds, auscultation of the bladder for determining urinary retention, respiratory sounds, and muscle sounds.

The power requirements and size of the components used in the electronic stethoscope system of the present invention allow the entire system to be battery operated and worn on the belt as a conventional transistorized radio.

If size and power requirements are not important factors, additional optional features can be added to the system. For example, a pulse separating gate can be added so that the input signal is analyzed only periodically. This gate is useful when it is desirable to analyze only particular periodic sounds, for example one of the four heart sounds. A signal enhancer can be added which enhances particular frequencies or assigns special chords, notes or note combinations to particular frequencies in order to produce a unique and distinctive set of sounds in the auditory range which easily indicate different kinds of pathology. Signal filters can be used to remove those frequencies which are undesirable.

The system can be used in conjunction with a device which obtains an electrocardiogram (ECG). The time varying waveform comprising the ECG is related to the electric fields generated in the body due to the spread of electrical excitation connected with the contraction cycle of the heart. The ECG waveform is normally interpreted by viewing the pattern on a paper chart. The system of the present invention can be used in conjunction with the normal ECG paper chart output by processing the ECG waveform to provide an audio signal corresponding to the ECG waveform in which frequencies not within the auditory range are translated into the auditory range.

The system can similarly be used with other waveforms including electroencephalogram (EEG) waveforms which are commonly used to diagnose brain and nervous system disorders, and electromyogram (EMG) waveforms which are used to assist patients with spinal chord or other nervous system disability to relearn motor control of their limbs.

Alternatively, a number of waveforms can simultaneously be applied to the system of the present invention with the translated version of each waveform being filtered so as to have frequencies within specified frequency ranges or alternatively each translated waveform can be assigned a particular chord, set of notes or note combinations.

The disclosed system can be connected to an additional information processor which, by using appropriate algorithms and stored data, will automatically interpret the enhanced sound to perform a medical diagnosis which can be displayed by a printed or video output or by the illumination of an appropriate indicator light.

Although the electronic stethoscope of the present invention is designed primarily to aid in medical diagnosis, it can also have non-medical uses such as, for example, a recreational device where users of the sound enhancement system can listen to musical tones or chords which correspond to their own bodily functions. In addition, the system can be used as an aid in other technical fields to enhance low or high frequency signals, for example, in testing the structural integrity of buildings and bridges and in detecting or predicting earthquakes.

BRIEF DESCRIPTION OF THE DRAWINGS

These and other objects, features and advantages of our invention will be more readily apparent from the following detailed description of a preferred embodiment of the invention in which:

FIG. 6a is a graphical representation of the frequency domain spectrum of sounds before processing, an FIG. 6b is a graphical representation after processing according to the system of the present invention.

DESCRIPTION OF THE PREFERRED EMBODIMENT

Figure 1:
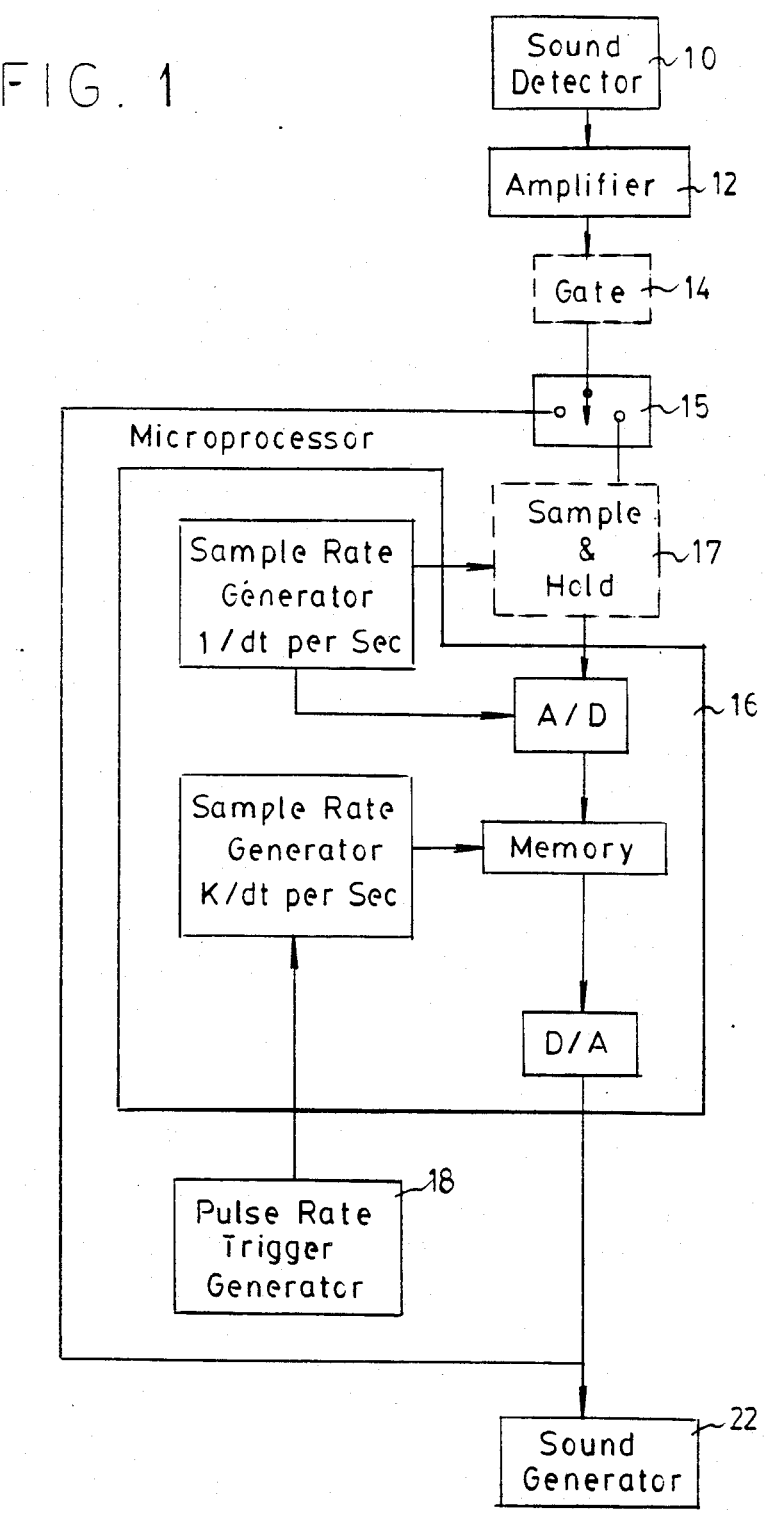
FIG. 1 is a schematic diagram of one embodiment of the system of the present invention.

FIG. 1 is a schematic diagram of a specific embodiment of the present invention where sound detected by a sound detector is electronically amplified and fed into a microprocessor where the frequency components of the sound are processed and then selectively enhanced. This processed signal is then filtered and converted into audible sound.

Referring to FIG. 1, sound detector 10 detects sound or acoustic vibrations emanating from a patient and converts the sound into an electrical signal. Sound detector 10 has a sensitivity such that it is able to detect sounds or acoustic vibrations having frequencies and intensities which are not within the auditory range of the human ear. Generally, the ear can hear sounds with frequencies as low as 20 Hz and as high as 20,000 Hz although at these extreme limits, the intensity range perceptible as sound is very small. A graphical representation of the auditory range of the human ear is shown in P.M. Morse, *Vibration And Sound*, Acoustical Society of America, 1976, page 227. Illustratively, sound detector 10 is a highly sensitive microphone or a stethoscope bell connected to an electronic circuit which converts the output of the stethoscope bell into an input electrical signal. The input electrical signal generated by sound detector 10 is amplified by amplifier 12 so that the entire frequency range of the detected sound is amplified.

The output of amplifier 12 is then optionally fed to gate 14 which periodically connects amplifier 12 to microprocessor 16. The amount of time $T_1$ that gate 14 connects amplifier 12 to microprocessor 16 as well as the time $T_2$ between these connections is preferably manually set by the operator. For example, when the electronic stethoscope system is used to monitor heart sounds, the gate connection period $T_1$ and separation time $T_2$ can be synchronized to the duration and beat frequency of a particular heart sound. The heart usually generates a series of two heart sounds although it may generate four sounds. The first sound occurs at the beginning of ventricular systole, its timing being revealed by the fact that it slightly precedes the rise of the carotid pulse. The second sound is a short sound and closely follows the closure of the two semilunar valves. The third sound occurs in early diastole, apparently at the time in which ventricular volume and compliance equilibrate. The fourth heart sound (presystolic or atrial sound) is related to atrial contraction and usually precedes the first heart sound but may occur in middiastole. A detailed discussion of these heart sounds is found in A.A. Luisada and G.S. Sainani; *A Primer of Cardiac Diagnosis;* W. H. Green, Inc.; 1968; pages 34-64. The waveform corresponding to each heart sound comprises a wave packet which is repeated with a period corresponding to the pulse rate of the heart.

Figure 2:
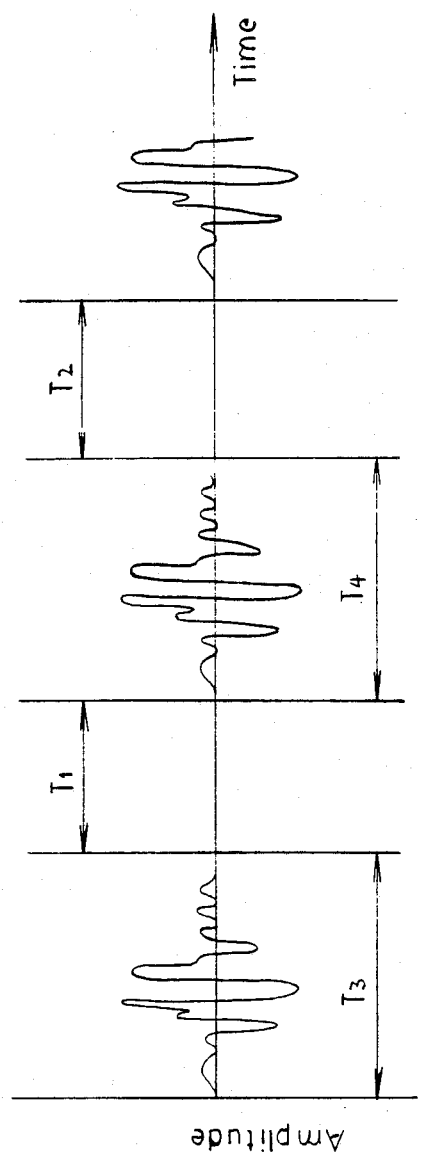
FIG. 2 is a graphical representation of the signal detected by the system of the present invention at one stage in its processing.

Referring to the operation of gate 14 of FIG. 1, the connection period $T_1$ and separation time $T_2$ can illustratively be selected so that only one of the heart sounds is detected. The output of gate 14 is thus in the form of a series of wave packets having a duration of $T_1$ seconds and separated by $T_2$ seconds as shown in FIG. 2. When gate 14 is used, single pole double throw switch 15 is provided between gate 14 and microprocessor 16. When the operator of the system is selecting gate connection period $T_1$ and separation time $T_2$, switch 15 connects gate 14 directly to sound generator 22, thereby by-passing microprocessor 16, so that the operator can determine when the correct values of $T_1$ and $T_2$ have been selected. Once $T_1$ and $T_2$ have been appropriately selected, switch 15 is switched so that gate 14 is connected to microprocessor 16. Thus, gate 14 periodically removes at least one wave packet (or heart sound) from the signal generated by amplifier 12. Although gate 14 is shown as separate from microprocessor 16, the operation performed by gate 14 can alternatively be performed by microprocessor 16. If gate 15 is not used, the output of amplifier 12 is optionally fed to a sample and hold circuit 17 and then to microprocessor 16.

Figure 3:
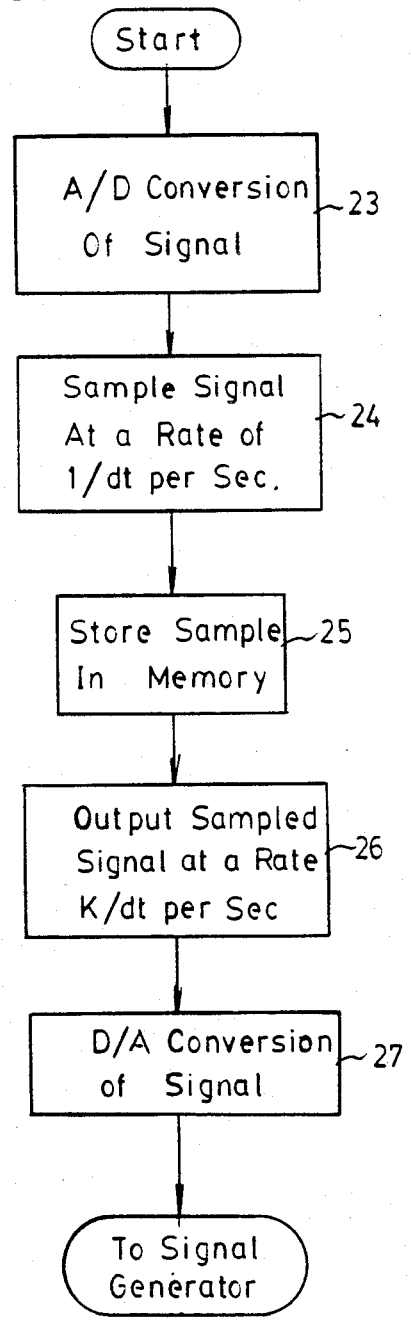
FIG. 3 is a flow diagram describing the operation of one embodiment of the system of the present invention.

The microprocessor 16 performs a number of mathematical operations on the signal generated by gate 14 to translate or time compress signals so that the inaudible sounds are translated into the auditory range. Referring to FIG. 1 and the flow chart in FIG. 3, the microprocessor first converts the input analog signal to a digital signal in block 23 at a predetermined sampling rate of 1/dt per second. Optionally the sampling may be done external to the microprocessor 16 by sample and hold circuit 17. Each sample is stored in memory as indicated by block 25. In block 26, the stored sample of the input signal is read from memory and output at a rate K times faster then the original sampling rate, where K is defined as the time scale compression factor. The original pulse rate is maintained by synchronizing the start of the output signal with the pulse rate. Preferably this is accomplished by an external pulse rate trigger 18 that may be manually adjusted to equal the pulse rate. The output signal is converted to an analog signal in block 27, and transmitted to the sound generator 22 for conversion of the electric signal into audible sounds. The sounds output from the sound generator maintain the same tonal relationships as the original heart sounds except at a higher pitch. A physician using the electronic stethoscope of this invention will recognize the different "melodies" heart sounds as well as hear those heart sounds which were previously inaudible.

Alternatively the analog to digital and digital to analog signal conversions may be performed external to the microprocessor 16. Illustratively, the microprocessor 16 is a CMOS microprocessor such as the 8 bit MC68HC11A4 microprocessor manufactured by Motorola Inc. of Schammburg, Ill., although other devices with similar capabilities can be used.

Figure 4:
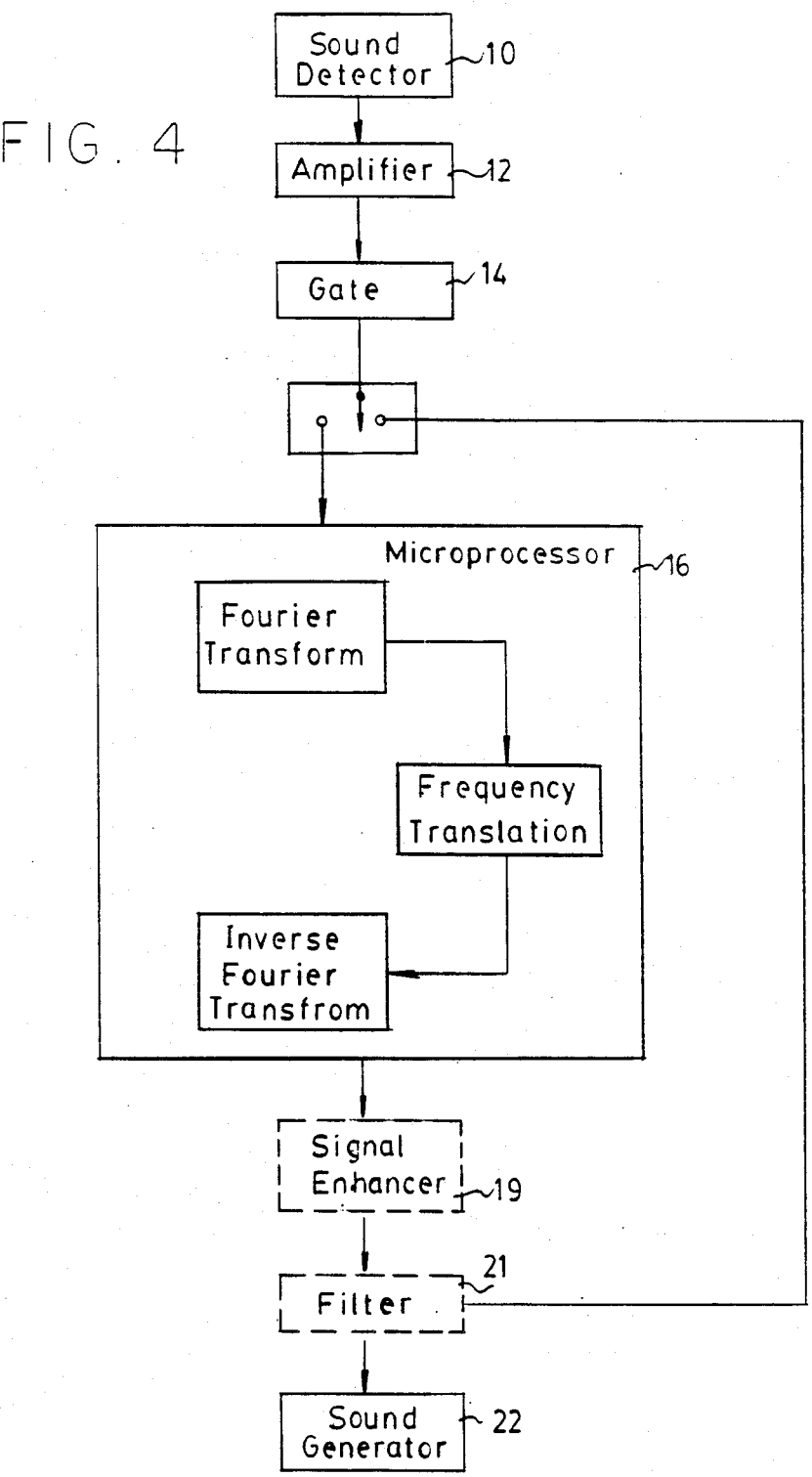
FIG. 4 is a schematic diagram of a second embodiment of the system of the present invention.

Another embodiment of the sound enhancement system of the present invention is illustrated in FIG. 4. The sound detected by a sound detector 10 is electronically amplified by amplifier 12 add fed into a microprocessor 16 where the signal is time compressed. The processed signal is then converted into audible sound.

As discussed in detail below with reference to the flow diagrams shown in FIGS. 5a and 5b, microprocessor 16 performs a number of mathematical operations on the signal generated by gate 14 to translate signals corresponding to inaudible sounds into the auditory range. Among the operations that microprocessor 16 performs are analog to digital conversion of the signal, signal sampling, Fourier transform, frequency translation, inverse Fourier transform, digital to analog conversion, and storage of information in temporary and permanent memory. Alternatively, analog to digital and digital to analog signal conversion can be performed external to microprocessor 16.

Optionally the output signal may be further enhanced. This further signal enhancement is preferably performed digitally by microprocessor 16 after the waveform has been translated in frequency and phase but before an inverse Fourier transform operation has been performed upon the translated signal. Such signal enhancement enhances the translated frequency signal either by amplifying particular frequency ranges or by assigning special chords, notes or note combinations to particular frequencies in order to produce a unique and distinctive output sound in the auditory range which can be correlated with standards of normal heart function or different kinds of pathology in heart function These unique sounds make the sound patterns which are related to various kinds of heart pathology more distinctive to the ear of the operator and hence easier to interpret. Although signal enhancement is preferably performed by microprocessor 16, the signal enhancement can alternatively be performed by signal enhancer 19 (shown in dashed lines) which receives the output electrical signal generated by microprocessor 16.

Similarly, the signal after frequency translation can be filtered digitally by microprocessor 16 to filter out those frequencies of sound that are undesirable. If the signal is to be filtered, this operation is preferably performed upon the translated signal while it is in the frequency domain prior to performing the inverse Fourier transform operation. Alternatively, signal filtering can be accomplished by analog filter 21 which receives the output of signal enhancer 19, or alternatively, microprocessor 16 if signal enhancer 19 is not used.

The output of filter 21 is used to drive sound generator 22 which produces sound or output vibrational waveform audible to the operator in response to the electrical signal from filter 21. Illustratively, sound generator 22 is a pair of earphones.

Figure 5A:
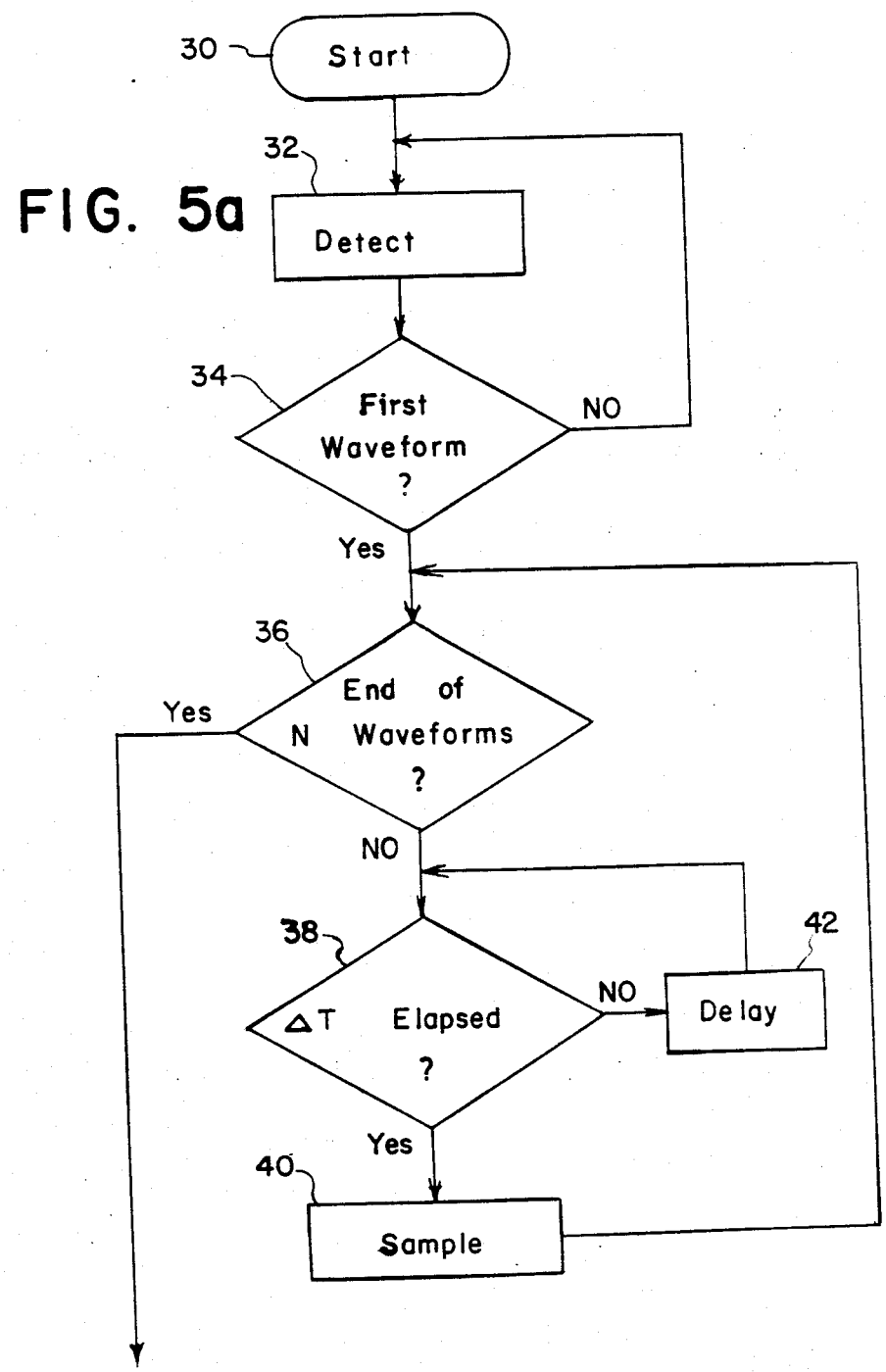
FIGS. 5a and 5b together are a flow diagram describing the operation of the second embodiment of the system of the present invention.
Figure 5B:
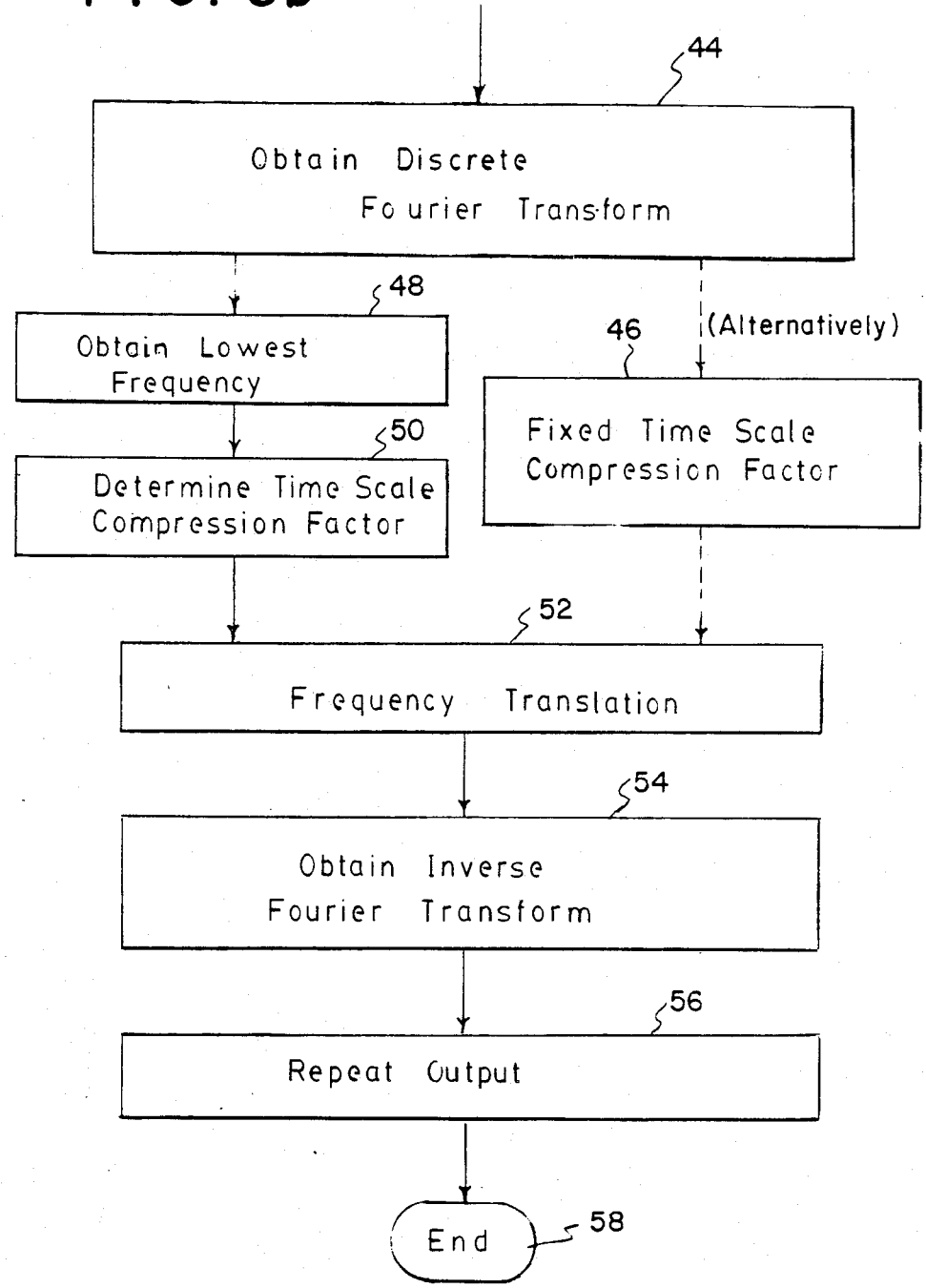

FIGS. 5a and 5b together show a preferred flow diagram describing the operation of microprocessor 16 of the embodiment of the present invention shown in FIG. 4. Referring to FIG. 5a, at block 30 the output generated by gate 14 is received by microprocessor 16. As previously discussed, when gate 14 is used, this signal is a series of wave packets separated by separation time periods as shown in FIG. 2. However, when gate 14 is not used and the sounds generated by the heart are being monitored, this signal is a series of wave packets not clearly separated by separation time periods. In block 32 this signal is detected by microprocessor 16 and converted from an analog signal to a digital signal.

In block 34, the beginning of a heart pulse is determined. Determining when the beginning of a heart pulse occurs can be performed manually by the operator by using a threshold detector with an appropriately set trigger level and by using a time delay generator. The trigger level of the threshold detector is manually set by the operator. In addition, the operator initially manually activates the threshold detector when the operator detects the beginning of a first heart pulse. Whenever the trigger level set by the operator is exceeded, a trigger pulse is generated and the time delay generator is triggered which generates a delay pulse which has a duration approximately equal to the expected time between heart pulses. Illustratively, the duration of the time delay pulse is about 750 milliseconds. The time delay pulse is used to inhibit the operation of the threshold detector As a result, the retriggering of the threshold detector is automatically prevented until the next heart pulse occurs. The duration of the delay pulse can alternatively be adjusted manually by the operator to accommodate different pulse rates. Illustratively, the time delay generator is a Schmitt trigger with a time delayed reset.

Alternatively, the beginning of heart pulses can be determined automatically. A peak detector is used to determine the maximum amplitude of the heart pulse waveforms. The trigger level of the threshold detector is then automatically set an arbitrary amount below this maximum amplitude. As is the case with manual operation, the operator must initially activate the threshold detector when the operator detects the beginning of a first heart pulse. The duration of the delay pulse produced by the time delay generator is determined automatically by determining the pulse rate period and setting the duration of the time delay pulse equal to an arbitrary amount below the pulse rate period. Appropriate use of discrete logic gates ensures that the threshold detector and time delay generator operate at the appropriate times. Thus, every time another heart pulse or wave packet is detected, another trigger pulse is automatically generated and a heart pulse counter is incremented by one.

In block 36, it is determined if a predetermined number N of heart pulses or wave packets, corresponding to the number of trigger pulses generated by the pulse generating means, have been detected by the heart pulse counter. If N pulses have not been detected, in block 38 it is determined whether the input electrical signal was sampled (in block 40), within the last dT seconds. If the previous pulse waveform sampling occurred within the last dT seconds, the sampling of the waveform is delayed a fixed period of time as shown by block 42. If the previous pulse waveform sampling occurred more than dT seconds previously, the input electrical signal is sampled as shown by block 40 and the amplitude of the sampled waveform is stored in the memory portion of microprocessor 16. As a result of the sampling loop of blocks 36, 38, 40 and 42, the input electrical signal comprising the N pulses is sampled every 1/dT seconds as shown by the dots in FIG. 7a and a sampled input electrical signal is obtained. Illustratively, dT is equal to 50 microseconds although other values for dT can be chosen. It is then redetermined in block 36 whether N pulses have been detected.

After N waveforms have been detected, a signal corresponding to the frequency spectrum of these sampled waveforms is obtained in block 44 as shown in FIG. 4b and stored in the memory of microprocessor 16. The frequency spectrum is preferably approximated by calculating the discrete Fourier transform (DFT) of the waveforms which describes the signal in real and imaginary components thus describing the frequency and phase of each component in the spectrum. This is accomplished by an algorithm generally known as a fast Fourier transform (FFT) which rapidly makes the computations required to obtain the DFT of an input signal. As a result of the FFT calculations, the continuous frequency spectrum of the input waveform signal is approximated by a series of points at different discrete frequencies having amplitudes which correspond to the amplitudes of the frequency spectrum at the different discrete frequencies. The sampled frequency spectrum signal obtained using the FFT operation is easily manipulated by performing mathematical operations on these frequency, phase and amplitude values as discussed in detail below.

Since an FFT approximation comprises both real and imaginary elements, thus taking into account both the frequency and phase elements of the signal, the operation of shifting the frequency spectrum up does not alter the phase and frequency relationships among the components in the spectrum. Therefore, the compressed waveform in the time domain maintains its original shape.

In order to translate components of sounds at or below the threshold of the auditory range of the human ear into the auditory range, according to the present invention, the frequencies and phase angles of these components are translated into the auditory range by time scale compression. Time scale compression is achieved by multiplying each of the discrete FFT values by a time scale compression factor. This time scale compression factor is chosen so that lower frequency components are translated to higher frequencies within the auditory range while other higher frequencies are translated so that they remain in the auditory range. The time scale compression factor can be preselected as indicated by block 46 or, alternatively, can be calculated, as shown in block 48 and block 50, based upon the lowest frequency component detected.

In block 48 the lowest (or base) frequency, F, is determined. The time scale compression factor, K, is determined in block 50 by dividing a standard frequency value, f, by the base frequency F. Thus, K=f/F. The standard frequency value f is chosen based upon an expected value for the base frequency so that the translated frequency spectrum remains within the auditory frequency range. Illustratively, the standard frequency value f is equal to about 15 Hz to about 30 Hz.

In block 52, each component of the sampled frequency spectrum signal obtained in block 44 is multiplied by the time scale compression factor K determined in block 46 or 50. As a result, each discrete FFT component detected is translated to a higher frequency by the same factor. This time scale compression or translation is shown in FIGS. 6a and 6b in which a simplified discrete frequency spectrum of the original waveform is shown in FIG. 6a while FIG. 6b shows the translated frequency spectrum of that shown in FIG. 6a wherein the amplitudes and relative inter-component frequency and phase relationships are maintained. Although the time scale compression factor K used to obtain the frequency spectrum of FIG. 6b from that shown in FIG. 6a is equal to 15, this value for K is only used as an example and other values for K can be used.

By using a time scale compression factor to uniformly translate the frequency and phase components of the original signal while maintaining the signal amplitude, the tonal relationship between the components remains unchanged. As shown in FIG. 6a, component 73 (50 Hz), component 74 (100 Hz) and component 75 (200 Hz) are separated by octaves. As shown in FIG. 6b their translated components, component 83 (750 Hz), component 84 (1500 Hz) and component 85 (3000 Hz), are also separated by octaves.

The relative inter-component phase relationship also remains constant. Thus, the tonal relationships in the original sound are maintained in the translated sound while the entire frequency spectrum is translated into the audible range.

At this point in the processing of the signal, as previously discussed with reference to FIG. 1, signal enhancement can optionally be performed digitally by microprocessor 16. Additionally, at this point the sampled translated frequency spectrum signal can be digitally filtered by microprocessor 16.

Returning to FIG. 5b, after the frequencies of the sampled frequency spectrum signal are translated in block 52, a time varying output electrical signal is obtained in block 54 by performing an inverse FFT operation on the translated signal.

The operations performed by microprocessor 16 can be described mathematically. If the original time varying input signal is f(t), its Fourier transform frequency spectrum shown in FIG. 6a is F($\omega$), and the translated frequency spectrum signal show in FIG. 6b is F'($\omega$), then $$F'(\omega) = F(\omega/K) \tag{1}$$

where K is the time scale compression factor. As is known from algebra, in order to translate the frequency spectrum F($\omega$) by a time scale compression factor K to obtain F'($\omega$), the frequency must be divided by the K as shown in equation (1) above.

By using the inverse Fourier transform operation, the time varying output signal $f_t(t)$ corresponding to the translated frequency spectrum signal F'($\omega$) is therefore:

$$f(t) = \frac{1}{2\pi} \int_{-\infty}^{+\infty} F(\omega) e^{j\omega t} d\omega \tag{2}$$

substituting equation (1) into equation (2) results in the following:

$$f(t) = \frac{1}{2\pi} \int_{-\infty}^{+\infty} F(\omega/K) e^{j\omega t} d\omega \tag{3}$$

If $\omega/K = \omega'$, then $\omega = K\omega'$, $d\omega = Kd\omega'$, and $$f(t) = \frac{1}{2\pi} \int_{-\infty}^{+\infty} F(\omega') e^{jK\omega' t} Kd\omega' \tag{4}$$

Taking the inverse Fourier transform of the right side of equation (4) results in the following:

$$f(t) = Kf(Kt) \tag{5}$$

Therefore, when each Fourier transform of the original signal is translated by multiplying each component by the time scale compression factor K, and if K is greater than one, the resulting varying output signal is equivalent to the time varying input signal compressed in time by a factor of K.

Preferably, the time varying output signal is then analyzed by microprocessor 16 to determine when heart pulses occur in the time scale compressed time varying output signal. The beginning of each pulse is then separated in time from the previous and next pulse to reestablish the timing of pulses present in the original time varying signal prior to time scale compression and processing. Alternatively, the timing of the heart pulses can be detected and the timing can be re-established by a means other than microprocessor 16, for example by the use of threshold detectors, time delay generators and discrete logic as discussed previously.

Returning to FIG. 5b, the time varying time scale compressed output signal is then optionally repeated a number of times as shown in block 56. At block 58 the signal is converted from a digital signal to an analog signal and is transmitted to signal enhancer 19, filter 21, and sound generator 22 shown in FIG. 4.

Figure 7A:
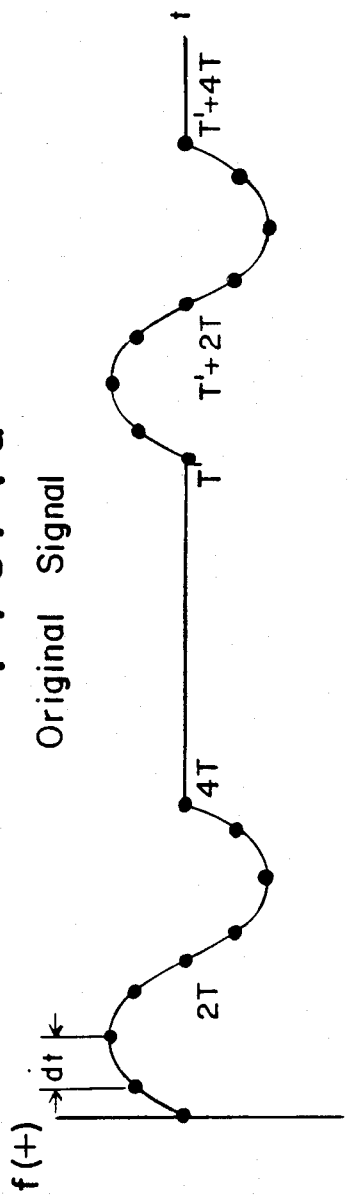
FIG. 7a is a graphical representation of signals in the time domain before enhancement.
Figure 7B:
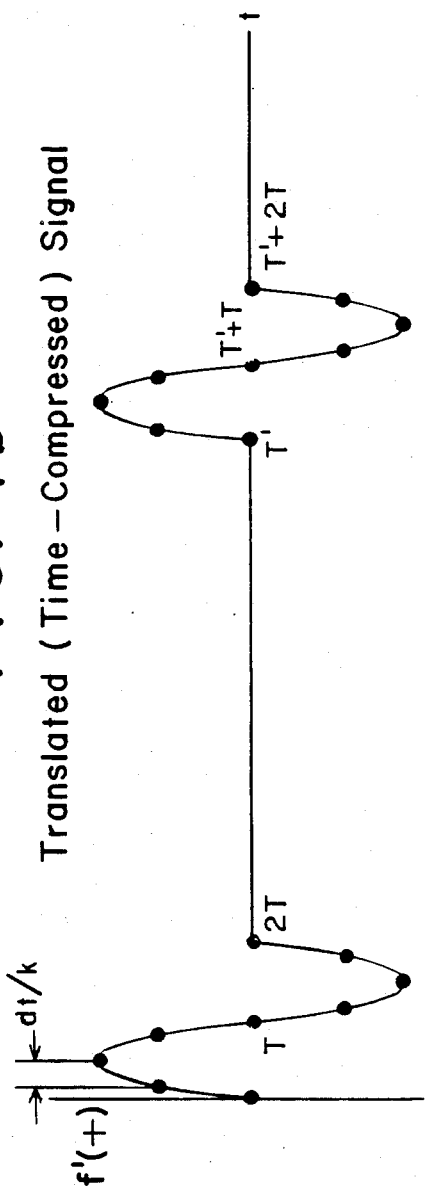
FIG. 7b is a graphical representation after enhancement according to the system of the present invention.

As mathematically shown above, translating low frequency components of a time varying signal into higher frequency range by a time scale compression factor maintains the tonal relationships in the original signal and is equivalent to compressing in time the original signal by a fixed factor. This is illustrated in FIGS. 7a and 7b in which 7a is the time varying input waveform and 7b is the time varying output waveform compressed in the time scale by a factor K, thereby maintaining the signal amplitude and relative frequency and phase relationships of the signal.

While the invention has been described in conjunction with specific embodiments, it is evident that numerous alternatives, modifications, variations, and uses will be apparent to those skilled in the art in light of the foregoing description.

What is claimed is:

1. A method for enhancing acoustic vibrations having frequency components that are not within the auditory range or the human ear comprising:
   detecting an input acoustic vibrational waveform within a first frequency range having frequency components that are not within the auditory range of the human ear, said frequency components having an intercomponent tonal relationship;
   converting said detected input acoustic vibrational waveform into an input electrical signal;
   performing a Fourier transform operation upon said input electrical signal, whereby an input frequency spectrum signal is obtained comprising frequency components, each frequency component comprising frequency, phase and amplitude elements, the frequencies of the frequency components comprising the a first inter-component frequency relationship and the phases of the frequency components comprising a first inter-component phase relationship;
   translating said input frequency spectrum signal in the time scale from said first frequency range to a second frequency range by multiplying said frequencies of the input frequency spectrum signal by a time scale compression factor, said frequency components of the translated frequency spectrum signal having a second inter-component frequency relationship and second inter-component phase relationship equivalent to the first inter-component frequency relationship and first inter-component phase relationship;
   performing an inverse Fourier transform operation on said translated frequency spectrum signal whereby an output electrical signal is obtained; and
   converting said output electrical signal into an output vibrational waveform having frequency components that are within the auditory range or the human ear and in which the inter-component tonal relationship is maintained.

2. The method of claim 1 further comprising:
   periodically sampling said input electrical signal prior to performing a Fourier transform on the input signal.

3. The method of claim 1 wherein:
   said input acoustic vibrational waveform is comprised of a series of at least two input wave packets having a period equal to an input packet period; and
   the method further comprising:
   processing said output electrical signal so that said output electrical signal is comprised of a series of at least two output wave packets having a period equal to said input packet period.

4. The method of claim 3 wherein at least one input wave packet is periodically removed from said input electrical signal prior to processing said input electrical signal.

5. The method of claim 1 wherein said time scale compression factor has a numeric value greater than one.

6. The method of claim 1 wherein said translated frequency spectrum signal is filtered prior to performing said inverse fast Fourier transform operation in order to remove certain frequency components from said translated frequency spectrum signal.

7. The method of claim 1 wherein said output electrical signal is filtered prior to converting said output electrical signal into said output vibrational waveform.

8. The method of claim 1 wherein certain components of said sampled translated frequency spectrum signal are enhanced prior to performing said inverse Fourier transform operation.

9. The method of claim 1 wherein certain frequencies of said output electrical signal are enhanced prior to converting said output electrical signal into said output vibrational waveform.

10. An apparatus for enhancing acoustic vibrations having frequencies that are not within the auditory range of the human ear comprising:
    means for detecting an input acoustic vibrational waveform within a first frequency range having frequencies that are not within the auditory range of the human ear, said frequencies having an inter-component tonal relationship;
    means for converting said detected input acoustic vibrational waveform to an input electrical signal;
    means for performing a Fourier transform operation upon said input electrical signal whereby an input frequency spectrum is obtained having a plurality of frequency components, each frequency component having frequency, phase and amplitude elements, the frequencies of the frequency components comprising a first inter-component frequency relationship and the phases of the frequency components comprising a first inter-component phase relationship;
    means for translating said frequency components of the input frequency spectrum to a frequency range within the auditory range of the human ear by multiplying said frequencies by a time scale compression factor, said frequency components of the translated frequency spectrum having a second inter-component frequency relationship and second inter-component phase relationship equivalent to said first intercomponent frequency relationship and first inter-component phase relationship;
    means for performing an inverse Fourier transform operation upon the translated frequency spectrum whereby an output electrical signal is obtained; and
    means for converting said output electrical signal into an output acoustic vibrational waveform, said output acoustic vibrational waveform having frequencies that are within the auditory range of the human ear and in which the inter-component total relationship is maintained.

11. The apparatus of claim 10 further comprising a means for periodically sampling said input electrical signal prior to inputting said signal into the means for performing a Fourier transform.

12. The apparatus of claim 10 wherein:
said input acoustic vibrational waveform is comprised of a series of at least two input waveform packets having a period equal to an input packet period; and
the apparatus further comprising:
means for processing said output electrical signal so that said output electrical signal is comprised of a series of at least two output wave packets having a period equal to said input packet period.

13. The apparatus of claim 12 further comprising gate means for periodically removing at least one input wave packet from said input electrical signal prior to processing said input electrical signal.

14. The apparatus of claim 10 wherein said time scale compression factor has a numeric value greater than one.

15. The apparatus of claim 10 further comprising means for filtering said translated frequency spectrum signal prior to performing said inverse Fourier transform operation in order to remove certain frequency components from said translated frequency spectrum signal.

16. The apparatus of claim 10 further comprising means for filtering said output electrical signal prior to converting said output electrical signal into said output vibrational waveform.

17. The apparatus of claim 10 further comprising frequency enhancing means for enhancing certain frequency components of said translated frequency spectrum signal prior to performing said inverse Fourier transform operation.

18. The apparatus of claim 10 further comprising frequency enhancing means for enhancing certain frequencies of said output electrical signal prior to converting said output electrical signal into said output vibrational waveform.

* * * * *